(12) United States Patent
Belzacq et al.

(10) Patent No.: US 9,958,347 B2
(45) Date of Patent: May 1, 2018

(54) ASSESSMENT OF SHEAR FORCES DISTRIBUTION AT FIXATION POINTS OF TEXTILE BASED IMPLANTS

(71) Applicant: Sofradim Production, Trévoux (FR)

(72) Inventors: Tristan Rene Guy Belzacq, Trevoux (FR); Clément Ordrenneau, Lyons (FR); Frédéric Laurent Pascal Turquier, Lyons (FR)

(73) Assignee: Sofradim Production, Trevoux (FR)

( * ) Notice: Subject to any disclaimer, the term of this patent is extended or adjusted under 35 U.S.C. 154(b) by 40 days.

(21) Appl. No.: 14/862,763

(22) Filed: Sep. 23, 2015

(65) Prior Publication Data

US 2016/0091375 A1    Mar. 31, 2016

(30) Foreign Application Priority Data

Sep. 30, 2014 (EP) .................... 14306543

(51) Int. Cl.
*G01L 5/00* (2006.01)
*A61F 2/00* (2006.01)
(Continued)

(52) U.S. Cl.
CPC .............. *G01L 5/00* (2013.01); *A61F 2/0063* (2013.01); *G01B 11/16* (2013.01); *G01N 3/068* (2013.01);
(Continued)

(58) Field of Classification Search
CPC ............ G01N 3/10; G01N 3/068; G01N 3/08; G01N 3/24; G01N 2203/0246; G01L 5/00; A61F 2/00; A61F 2/0063; G01B 11/16
(Continued)

(56) References Cited

U.S. PATENT DOCUMENTS 3,541,843 A    11/1970  Flesher
3,580,050 A     5/1971  Waldron
(Continued)

FOREIGN PATENT DOCUMENTS

GB         2 389 665 A     12/2003
WO    WO 2005/054815 A1    6/2005
WO    WO 2014/115130 A2    7/2014

OTHER PUBLICATIONS

European Search Report for EP 14306543.1-1553 date of completion is Mar. 13, 2015 (9 pages).
(Continued)

*Primary Examiner* — Harshad R Patel
*Assistant Examiner* — Octavia Hollington (57) ABSTRACT

A system for assessing the distribution of shear forces at fixation points on a textile-based implant includes a tissue model, a load simulation device, and an analysis system. The tissue model includes an upper surface defining an opening therethrough and a fixation support configured to secure a textile-based implant against the upper surface at a plurality of fixation points defined along a plane of the upper surface. The load simulation device is configured to apply a load to a textile-based implant that is secured to the tissue model. A marker is disposed on the fixation support at one or more of the plurality of fixation points. The analysis system is configured to calculate a shear force vector at each of the fixation points where a marker is disposed in response to the load applied by the load simulation device.

17 Claims, 3 Drawing Sheets (51) Int. Cl.
*G01N 3/24* (2006.01)
*G01B 11/16* (2006.01)
*G01N 3/06* (2006.01)
*G01N 3/08* (2006.01)
*G01N 33/36* (2006.01)

(52) U.S. Cl.
CPC .............. *G01N 3/08* (2013.01); *G01N 3/24* (2013.01); *A61F 2240/008* (2013.01); *G01N 33/367* (2013.01); *G01N 2203/0282* (2013.01); *G01N 2203/0494* (2013.01); *G01N 2203/0647* (2013.01)

(58) Field of Classification Search
USPC ........................................................ 73/804
See application file for complete search history.

(56) References Cited

U.S. PATENT DOCUMENTS

| | | | |
|---|---|---|---|
| 3,807,224 A | | 4/1974 | Hassenboehler |
| 4,677,854 A | | 7/1987 | Gabelli |
| 6,162,962 A | | 12/2000 | Hinsch et al. |
| 6,177,940 B1 | | 1/2001 | Bond et al. |
| 7,371,067 B2 | | 5/2008 | Anderson et al. |
| 7,556,045 B1 | | 7/2009 | Recknor et al. |
| 7,762,146 B2 | * | 7/2010 | Brodland ................ G01N 3/04 |
| | | | 73/826 |
| 8,246,663 B2 | | 8/2012 | Lovald et al. |
| 8,297,982 B2 | | 10/2012 | Park et al. |
| 8,606,591 B2 | | 12/2013 | Heniford et al. |
| 8,775,133 B2 | | 7/2014 | Schroeder |
| 9,134,209 B2 | * | 9/2015 | Brodland ................ G01N 3/04 |
| 2013/0125663 A1 | | 5/2013 | Hasegawa et al. |
| 2013/0231911 A1 | | 9/2013 | Brown et al. |
| 2016/0157981 A1 | * | 6/2016 | Lecuivre ................ D04B 1/22 |
| | | | 606/151 |

OTHER PUBLICATIONS

Zioupos P et al: "Mechanical and Optical Anisotropy of Bovine Pericardium", Medical and Biological Engineering and Computing, Springer, Heildelberg, DE, vol. 30, No. 1, Jan. 1, 1992 (Jan. 1, 1992), pp. 76-82, XP000246241.

* cited by examiner

ASSESSMENT OF SHEAR FORCES DISTRIBUTION AT FIXATION POINTS OF TEXTILE BASED IMPLANTS

CROSS-REFERENCE TO RELATED APPLICATIONS

This application claims benefit of and priority to European Patent Application Serial No. 14306543.1 filed Sep. 30, 2014, the disclosure of the above-identified application is hereby incorporated by reference in its entirety.

TECHNICAL FIELD

The present disclosure relates to textile-based implants, and more particularly, to experimental systems, devices, and methods for assessing the distribution of shear forces at fixation points of textile-based implants.

BACKGROUND

Techniques for repairing damaged or diseased tissue are widespread in medicine. Wound closure devices, such as sutures, staples, and tacks, as well as tissue reinforcements/replacement devices like meshes and patches, are frequently used for repair. For example, in the case of abdominal wall hernias, techniques involving the use of a mesh or patch to reinforce the abdominal wall are used. The mesh or patch is generally soft and pliant in order to conform to the abdominal wall and flex with movement of the abdominal wall. The mesh or patch may be held in place by suturing, stapling, or tacking the mesh or patch to surrounding tissue.

The performance of the abdominal wall hernia repair using a mesh or patch fixed on the abdominal wall depends in part upon the shear forces experienced at the mesh or patch fixation points. These shear forces may be quite high as a result of high intra-abdominal pressure. It would be advantageous therefore to measure and evaluate the distribution of shear forces at fixation points of a mesh or patch under physiological loads.

SUMMARY

The present disclosure is directed to experimental systems, devices, and methods for assessing the distribution of shear forces at fixation points of textile-based implants to reduce the likelihood of implant failure or fixation pull out.

In one aspect of the present disclosure, a system for assessing the distribution of shear forces at fixation points on a textile-based implant includes a tissue model, a load simulation device, and an analysis system. The tissue model includes an upper surface extending along a plane and defining an opening therethrough, and a fixation support configured to secure a textile-based implant against the upper surface at a plurality of fixation points defined along the plane of the upper surface. The load simulation device is configured to apply a load to a textile-based implant secured to the tissue model. At least one marker is disposed on the fixation support at one or more of the plurality of fixation points. The analysis system is configured to calculate a shear force vector at each of the one or more of the plurality of fixation points where the at least one marker is disposed in response to the load applied by the load simulation device.

In another aspect of the present disclosure, a method of measuring shear forces distribution at fixation points of a textile based implant includes: securing a textile-based implant to a fixation support of a tissue model to create at least two fixation points defined along a plane of an upper surface of the tissue model; placing at least one marker on the fixation support at one or more of the at least two fixation points; subjecting the textile-based implant to a load; and measuring the displacement of the at least one marker and calculating the shear force vector at each of the one or more of the at least two fixation points where the at least one marker is disposed in response to the load.

Other aspects, features, and advantages will be apparent from the description, drawings, and the claims.

BRIEF DESCRIPTION OF THE DRAWINGS

Embodiments of the presently disclosed system are described herein with reference to the drawings, wherein.

Corresponding reference characters indicate corresponding parts throughout the drawings.

DETAILED DESCRIPTION

For the purposes of discussion, the systems, devices, and methods for assessing shear forces distribution at fixation points of textile-based implants will be described with respect to an abdominal wall model including a hernia defect configured to simulate an active abdominal wall, and the effects of simulated intra-abdominal pressure on a surgical mesh attached to the abdominal wall model. It should be understood, however, that the presently disclosed systems, devices, and methods may be utilized with any textile-based implant suitable for use in a surgical application including tissue having open defects.

Figure 1:
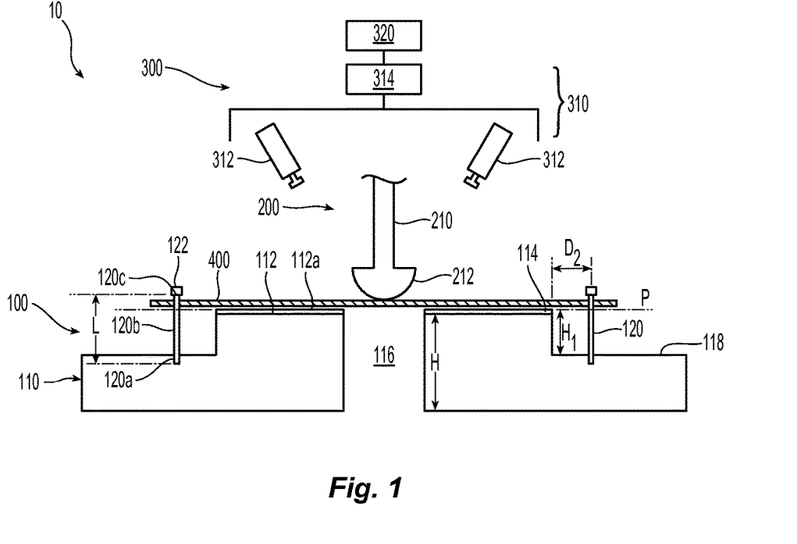
FIG. 1 is a side view illustrating a schematic configuration of a system in accordance with an embodiment of the present disclosure.
Figure 2:
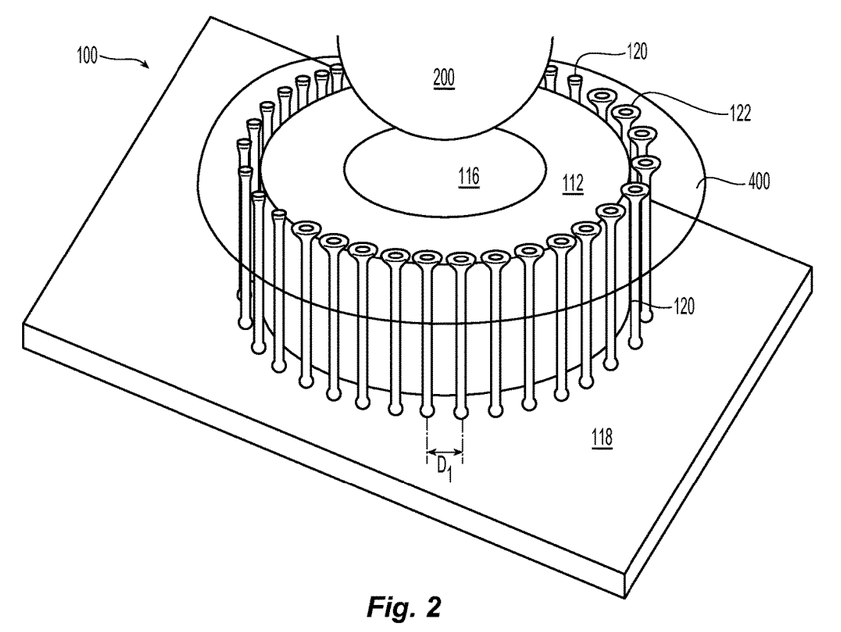
FIG. 2 is an enlarged, perspective view of a portion of the system of FIG. 1.

Referring now to FIGS. 1 and 2, a system 10 includes a tissue model 100, a load simulation device 200, and an analysis system 300 for assessing characteristics of a textile-based implant 400 when fixed to the tissue model 100 and subjected to a load exerted by the load simulation device 200. The tissue model 100 includes a base 110 having an upper surface 112 extending along a plane "P" and having a closed outer perimeter 114 that defines an opening 116 therethrough. The upper surface 112 is configured to mimic the inner surface of an abdominal wall and may be referred to herein as the "inner surface abdominal wall equivalent". The opening 116 defined through the upper surface 112 is configured to mimic a defect in an abdominal wall and may be referred to herein as the "defect". While the opening 116 is shown as having a circular shape and a uniform size and dimension through the height "H" of the base 110, it should be understood that the opening 116 may be of any shape and size, and may vary in dimension through the height "H" of the base 110. In embodiments, the opening may be non-circular, such as oval, oblong, rectangular, polygonal, as well as elongated and/or non-uniform shapes (e.g., shapes formed from incisions, punctures, etc.).

In embodiments, the upper surface 112 may include a coating, film, or other material covering 112a having a coefficient of friction that mimics the frictional coefficient of the "inner surface abdominal wall equivalent" 112 against a textile-based implant 400. Such materials include, for example, lubricants, oils, waxes, and films. In embodiments, the coefficient of friction is about 0.1 to about 0.3.

The base 110 includes a lower surface 118 that is stepped down from the upper surface 112 at a pre-determined height "$H_1$" and extends around the upper surface 112. While the upper and lower surfaces 112 and 118 are shown as planar surfaces, it should be understood that the upper surface 112 and/or the lower surface 118 may be non-planar, such as curved, wavy, or other configurations that mimic the tissue being modeled.

The base 110 also includes a fixation support, such as a plurality of rods 120, configured to secure a textile-based implant 400 thereto at two or more fixation points. The plurality of rods 120 are attached to the lower surface 118 at a predetermined distance "$D_1$" from each other and a predetermined distance "$D_2$" from the upper surface 112 extremity. The rods 120 may be arranged in any fixation pattern utilized in a surgical procedure, such as, for example, single or double crown fixation. Each rod 120 includes a first end 120a fixed to the lower surface 118, an elongate body 120b extending from the lower surface 118 towards the upper surface 112 and defining a length "L", and a second end 120c terminating about or above the plane "P" defined by the upper surface 112. In embodiments, the elongate body 120b extends perpendicularly from the lower surface 118. In other embodiments the fixation support could be made of foam or other resilient materials.

The rods 120 are configured for direct fixation to a portion of the textile-based implant 400 when the textile-based implant 400 is placed upon the upper surface 112 of the tissue model 100 over the opening 116 in the upper surface 112. It should be understood, however, that fixation devices, such as sutures, tacks, and/or staples, may be utilized to fix the implant 400 to the rods 120. A mechanical link between the rods 120 and the lower surface 118, and/or an adjustment of the angle between the rods 120 and the lower surface 118, may be used to apply negative or positive tension at the fixation points in the textile-based implant 400. Markers 122 may be attached to the second end 120c of the rods 120 such that the markers 122 are disposed about or above the plane "P" defined by the upper surface 112. Markers 122 provide a visual indication of the position of the rods 120. Markers 122 may be provided on all, or a portion, of the rods 120.

The load simulation device 200 is positioned above the upper surface 112 of the base 110 and is configured to simulate a change in environmental loading conditions surrounding the tissue model 100 such that changes in load are generated about the tissue model 100. The load may be referred to herein as the "intra abdominal pressure equivalent." As shown, the load simulation device 200 is a plunger 210 including a contacting surface 212 that is centered over the opening 116 defined through the upper surface 112. The contacting surface 212 may have any shape, such as spherical, hemispherical, conical, as well as other non-planar shapes, or may be planar. The plunger 210 is configured to move in a direction perpendicular to the plane "P" of the upper surface 112 and exert a predetermined force against the textile-based implant 400 so that the implant 400 engages the opening 116 defined within the upper surface 112 of the tissue model 100. Additionally or alternatively, the plunger 210 may be configured to move at non-perpendicular angles relative to the plane "P" of the upper surface 112. It should be understood, however, that the load simulation device 200 may be any mechanical or electromechanical device, pressure source, and/or electromagnetic field generating device capable of applying a static, quasi-static, or dynamic pressure on the implant 400 to simulate various physiological conditions.

The analysis system 300 includes a digital image acquisition and processing component 310 including two or more cameras 312 for recording the position of the markers 122 in a 3D coordinate system and digital image correlation software 314 for calculating the displacement vector of each of the markers 122 resulting from bending of the rods 120 due to movement of the implant 400 in response to the loads exerted on the implant 400 by the load simulation device 200. The analysis system 300 records the plunger displacement 210. The analysis system 300 also includes a mathematical software component 320 that is utilized to calculate the shear force vector at each fixation point where a marker 122 exists using the displacement vector component in the plane "P" of the markers 122 and the continuum mechanics theory applied to the rods 120. Accordingly, each shear force vector is a function of the "intra abdominal pressure equivalent." The mathematical software component 320 may include any numerical software package, such as, for example, MATLAB®. It should be understood that the shear force vector can be calculated using any marker type and location, and any computational analysis system configured to measure and analyze positional change in the markers.

In addition, any corresponding bulging of the textile-based implant 400 through the opening 116 may also be assessed, provided that any rod deflection contribution is subtracted from the calculation. The rod deflection contribution may be calculated by the analysis system 300. In embodiments, the rod deflection contribution is calculated using a mathematical equation transforming the layout area defined by two perimeters interpolating the position of the fixation points, one at the initial, load-free state and the other under load when the rods are bent. In embodiments, the rod deflection contribution is calculated using a superposition experimental method which includes evaluating the residual textile-based implant engagement when the fixation points are moved to the fixation points positions under load when the rods are bent.

In an exemplary method of use, a textile-based implant 400, such as a surgical mesh, is placed on the upper surface 112 of the base 110 of the tissue model 100 such that the implant 400 lies along the plane "P" defined by the upper surface 112. The implant 400 is centered placed about the opening 116 in the upper surface 112 and, as should be understood by a person of ordinary skill in the art, the orientation of the fibers of the implant 400 is controlled with respect to the upper surface 112. The textile-based implant 400 is then directly fixed to the plurality of fixation rods 120. A plurality of markers 122 are then affixed to a portion of the fixation rods 120 such that the markers 122 extend between the two warp extremities of the implant 400.

With the implant 400 fixed to the tissue model 100, the analysis system 300 is activated such that the cameras 312 captures the position of the markers 122 in a 3D coordinate system. The acquisition of the position/positional changes of the markers 122 via the cameras 312 is synchronized with the activation of the load simulation device 200 as the forces applied to the implant 400 by the load simulation device 200 is transferred to the rods 120 at the fixation points and results in bending of the rods 120. Accordingly, any movement of the rods 120 results in movement of the markers 122 which is recorded by the cameras 312 and used in determining the shear force vector at each fixation point as described above.

As described in the examples below, the system of the present disclosure may be utilized to assess the performance of textile-based implants in tissue models having a non-closed defect under various simulated physiological conditions. Such systems may be utilized to assess the shear forces distribution profile at fixation points of textile-based implants under various simulated physiological conditions to aid in choosing an appropriate textile-based implant for surgical use.

EXAMPLES

Example 1—Intra/Pre-Peritoneal Abdominal Wall Hernia Repair Equivalent System

A test was designed to assess the shear forces at mesh fixation points for an "intra/pre-peritoneal abdominal wall hernia repair equivalent" system set-up. The system is described in Table 1, the system means of measure are described in Table 2, and the system results are described in Table 3.

TABLE 1

System set-up parameters

| System Designation | Parameters |
|---|---|
| Tissue Model | "Inner surface abdominal wall equivalent" geometry and material properties |
| | "Defect" geometry and material properties |
| | Friction coefficient contact between the "inner surface abdominal wall equivalent" and a textile-based implant |
| | Rod links |
| | Environment |
| Load Simulation Device | Loading conditions |
| | Regime |
| | Value |
| Medical Devices | Textile-based implant |
| | Fixation means |
| Surgical technique | Fixation distribution |
| | Pre-tension (negative or positive) at fixation points in the textile based implant |

TABLE 2

System means of measure parameters

| System Designation | Parameters |
|---|---|
| Means of measure | Rod properties |
| | Marker properties |
| | Displacement calculation system |
| | Continuum mechanics theory applied to rods |
| | Fixation numbering |

TABLE 3

System results parameters

| System designation | Parameters |
|---|---|
| Shear Forces Distribution | Shear force vector at each fixation point where markers exist from the initial fixation position |
| | Vector scale |
| | Max and min vector norm values |
| Bulging | Textile-based implant engagement in the "defect" without subtracting the engagement resulting from rod displacements |
| Rupture of textile at fixation | Rupture at fixation reported by the fixation numbering |

Example 2—Shear Forces Distribution Assessment

Figure 3:
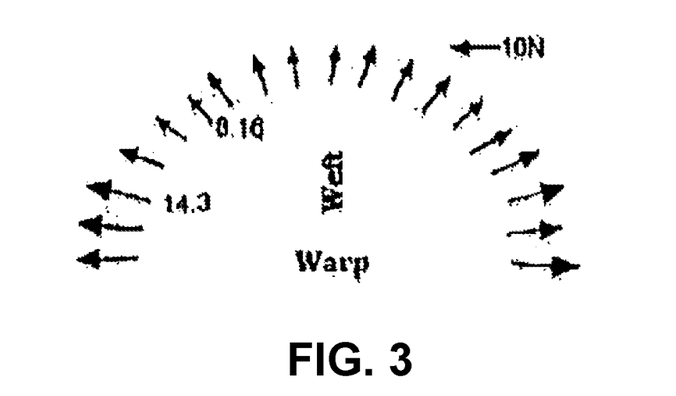
FIG. 3 is a schematic view of response to the shear forces distribution test of Table 6.

The system of Example 1 was utilized with the chosen variables for the system set-up and the system means of measure identified in Tables 4 and 5 below. FIGS. 1 and 2 illustrate the corresponding system set-up and system means of measure. The system response of the test is provided in Table 6. FIG. 3 illustrates a corresponding response to the shear forces distribution of Table 6.

TABLE 4

System set-up parameters

| System Designation | Parameters | Chosen Variable(s) |
|---|---|---|
| Tissue Model | "Inner surface abdominal wall equivalent" geometry and material properties | Flat Horizontal |
| | "Defect" geometry and material properties | Empty Circle: with 10 mm fillet radius: 55 mm |
| | Friction coefficient contact between the "inner surface abdominal wall equivalent" and a textile-based implant | Lino coating |
| | Rod links | Fixed |
| | Environment | Open air |
| Load Simulation Device | Loading conditions | Spherical plunger contact centered to the "defect" diameter: 100 mm |
| | Regime | Static |
| | Value | Plunger Force: 304N |
| Medical devices | Textile based implant | Covidien Symbotex ™ Composite Mesh (Type 3DS) Circle, diameter: 250 mm |
| | Fixation means | Mesh directly fixed to rods |
| Surgical technique | Fixation distribution | Simple circle crown, centered to the "defect" diameter: 230 mm overlap: 70 mm equal fixation distance from each other: 20 mm |
| | Tension at fixation points in the textile based implant | Minimum tension |

TABLE 5

System means of measure parameters

| System Designation | Parameters | Chosen Variable(s) |
|---|---|---|
| Means of Measure | Rod properties | Threaded rod M3, equivalent radius: 2.5 mm Length: 69 mm Material properties, Young Modulus: 110 Gpa |
| | Marker properties | Marker Type: white circle within black circle black circle diameter: 10 mm white circle diameter: 5 mm Localization: 3 mm above the textile-based implant Marker distribution: on half from two warp extremities |
| | Displacement calculation system | Digital image correlation system: Vic 3D ™ |
| | Continuum mechanics theory applied to rods | Bending beam model Bernoulli |
| | Fixation numbering | Consecutive |

TABLE 6

System results parameters

| System designation | Parameters | Response |
|---|---|---|
| Shear Forces Distribution | Shear force vector at each fixation point where markers exist from the initial fixation position<br>Vector scale<br>Max and min vector norm values | |
| Bulging | Textile-based implant engagement in the "defect" | Bulging indication without the rod deflection contribution subtraction: 48.9 mm |
| Rupture of textile at fixation | Rupture at fixation are reported by the fixation numbering | None |

Figure 4:
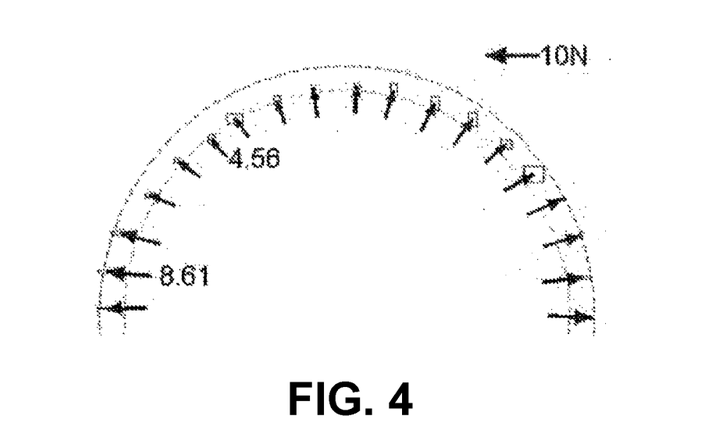
FIGS. 4 and 5 are a schematic view of the shear force vectors of tests with plunger force of 147 N and 304 N, respectively.
Figure 5:
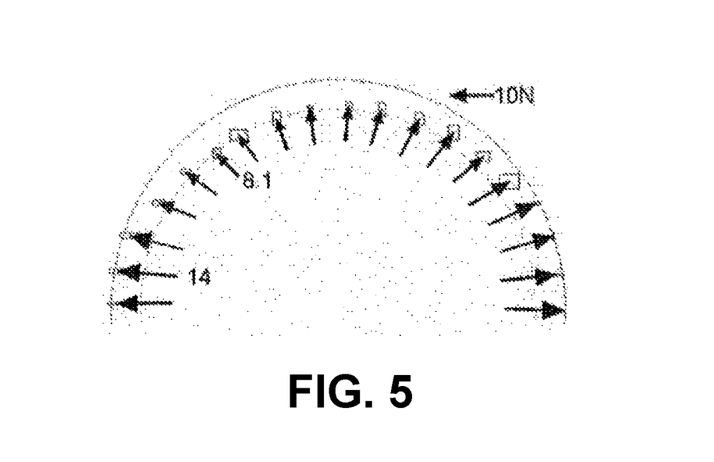
Figure 6:
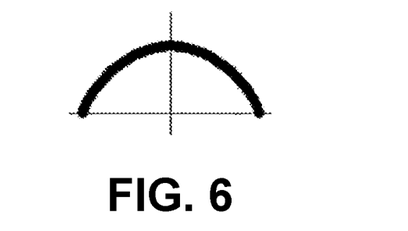
FIGS. 6-10 are schematized shear force vector distribution profiles of the surgical mesh in Table 8.
Figure 7:
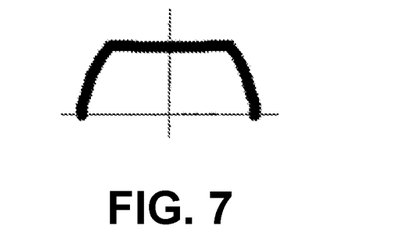
Figure 8:
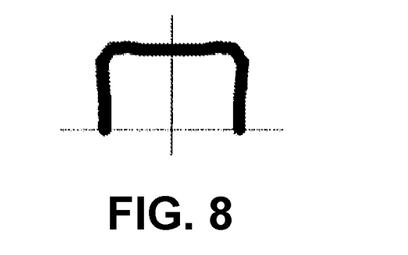
Figure 9:
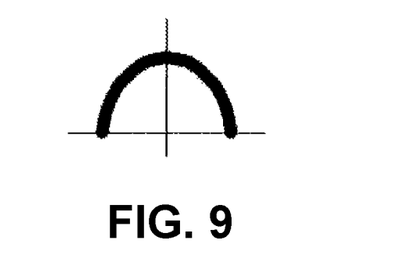
Figure 10:
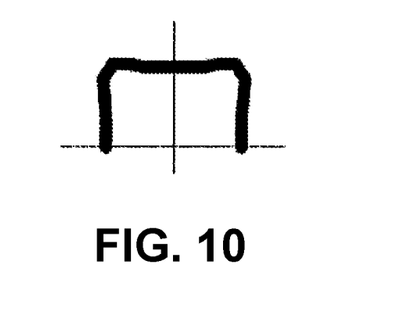

The test was repeated three times at a plunger force of 147 N and 304 N, and the resulted averaged. The pressure indication on the mesh was equal to the applied force divided by the size of the defect. The results, including the bulging indication and shear force vectors at each fixation point including a marker, are provided in Table 7 below and FIGS. 4 (plunger force 147 N) and 5 (plunger force 304 N).

TABLE 7

Results

| Plunger Force: | 147N | Plunger Force: | 304N |
|---|---|---|---|
| Pressure Indication: | 116 mm Hg | Pressure Indication: | 240 mm Hg |
| Bulging Indication: | 42.1 mm | Bulging Indication: | 49.3 mm |

Example 3—Comparison of Surgical Meshes

Table 8 below provides a response comparison of the various commercially available surgical meshes that were subjected to the system set-up and testing method of Example 2. FIGS. 6-10 illustrate a corresponding shear force vector distribution profile for each of the surgical meshes of Table 8.

TABLE 8

Comparison of Surgical Meshes

| Textile | Suture Pull-out Strength (N) | Plunger Force (N) | Pressure (mmHg) | Avg. bulging indication (mm) | Force Min-Max (N) | Shear-Force Vector Distribution Profile |
|---|---|---|---|---|---|---|
| Symbotex ™ Composite Mesh | 39 (warp) 44 (weft) | 147 | 116 | 42.1 | 4.56-8.61 | |
| | | 304 | 240 | 49.3 | 8.1-14 | |
| Parietex ™ Composite Mesh | 26 warp) 31 (weft) | 147 | 116 | 31.1 | 2.3-7.3 | |
| | | 304 | 240 | 39 | 4.4-11.7 | |
| Parietene ™ Composite Mesh | 57 (warp) 55 (weft) | 147 | 116 | 41.8 | 4-7.1 | |
| | | 304 | 240 | 50.3 | 6.6-11.8 | |
| Parietex ™ Light Weight Mesh | 31 (warp) 36 (weft) | 147 | 116 | 48 | 3.9-4.8 | |
| | | 304 | 240 | 58.7 | 6.5-8.6 | |
| Parietene ™ Light Weight Mesh | 37 (warp) 30 (weft) | 147 | 116 | 44.6 | 2.7-5.7 | |
| | | 304 | 240 | 54.5 | 4.5-11.2 | |

A number of embodiments have been described. Nevertheless, it will be understood that various modifications may be made without departing from the spirit and scope of the disclosure. Accordingly, other embodiments are within the scope of the following claims.

The invention may be described by reference to the following numbered paragraphs:

1. A system for assessing the distribution of shear forces at fixation points on a textile-based implant, the system comprising:
   a tissue model including an upper surface extending along a plane and defining an opening therethrough, and a fixation support configured to secure a textile-based implant against the upper surface at a plurality of fixation points defined along the plane of the upper surface;
   a load simulation device configured to apply a load to a textile-based implant secured to the tissue model;
   at least one marker disposed on the fixation support at one or more of the plurality of fixation points; and
   an analysis system configured to calculate a shear force vector at each of the one or more of the plurality of fixation points where the at least one marker is disposed in response to the load applied by the load simulation device.

2. The system of paragraph 1, wherein the upper surface includes a coating to mimic the coefficient of friction between an abdominal wall and a textile-based implant.

3. The system of paragraph 1, wherein the fixation support includes a plurality of rods, each rod including a first end fixed to a lower surface of the tissue model that extends around the upper surface of the tissue model, and a second end terminating about or above the plane of the upper surface.

4. The system of paragraph 3, wherein the at least one marker is disposed on the second end of one or more of the plurality of rods.

5. The system of paragraph 3, wherein each rod of the plurality of rods is positioned in a 3D coordinate system in relation to a barycenter of the opening in the upper surface of the tissue model.

6. The system of paragraph 3, wherein each rod of the plurality of rods is uniformly spaced a predetermined distance apart from an adjacent rod of the plurality of rods and a predetermined distance from the upper surface of the tissue model.

7. The system of paragraph 1, wherein the at least one marker is disposed on the fixation support at fixation points positioned at two warp extremities of the textile-based implant.

8. The system of paragraph 1, wherein the load simulation device is a plunger including a spherical contacting surface.

9. The system of paragraph 8, wherein the plunger is configured to exert a force in a direction perpendicular to the plane of the upper surface of the tissue model.

10. The system of paragraph 1, wherein the analysis system includes a digital image acquisition and processing component including two or more cameras for recording the position of the at least one marker in a 3D coordinate system and digital image correlation software for calculating a displacement vector of the at least one marker.

11. The system of paragraph 10, wherein the analysis system includes mathematical software for calculating the shear force vector using the displacement vector of the at least one marker.

12. The system of paragraph 1, wherein the analysis system is configured to control the load simulation device.

13. The system of paragraph 12, wherein the analysis system is configured to calculate a bulge in the textile-based implant.

14. A method of measuring shear forces distribution at fixation points of a textile based implant, the method comprising:
securing a textile-based implant to a fixation support of a tissue model to create at least two fixation points defined along a plane of an upper surface of the tissue model;
placing at least one marker on the fixation support at one or more of the at least two fixation points;
subjecting the textile-based implant to a load; and
measuring the displacement of the at least one marker and calculating a shear force vector at each of the one or more of the at least two fixation points where the at least one marker is disposed in response to the load.

15. The method of paragraph 14, wherein securing a textile-based implant includes placing a textile-based implant over an opening defined through the upper surface of the tissue model.

16. The method of paragraph 14, wherein the fixation support includes a plurality of rods extending from a lower surface of the tissue model and disposed around the upper surface of the tissue model, and wherein placing at least one marker includes positioning the at least one marker on one or more of the plurality of rods.

17. The method of paragraph 16, wherein securing a textile-based implant includes directly fixing a textile-based implant to the plurality of rods.

18. The method of paragraph 16, wherein placing at least one marker includes securing markers to rods of the plurality of rods positioned at two warp extremities of the implant.

19. The method of paragraph 14, further comprising activating cameras to capture an initial position of the at least one marker in a 3D coordinate system prior to subjecting the textile-based implant to a load and wherein measuring the displacement of the at least one marker includes capturing positional changes of the at least one marker with the cameras after subjecting the textile-based implant to the load.

20. The method of paragraph 19, wherein subjecting a textile-based implant to a load includes activating a load simulation device.

21. The method of paragraph 20, wherein capturing positional changes of the at least one marker is synchronized with activating the load simulation device.

22. The method of paragraph 19, wherein measuring the displacement of the at least one marker further includes calculating a displacement vector for the at least one marker.

23. The method of paragraph 22, further comprising calculating a bulge in the textile-based implant.

What is claimed is:

1. A system for assessing the distribution of shear forces at fixation points on a textile based implant, the system comprising:
a tissue model including an upper surface extending along a plane and defining an opening therethrough, and a fixation support configured to secure a textile-based implant against the upper surface at a plurality of fixation points defined along the plane of the upper surface;
a load simulation device configured to apply a load to a textile-based implant secured to the tissue model;
at least one marker disposed on the fixation support at one or more of the plurality of fixation points; and
an analysis system configured to calculate a shear force vector at each of the one or more of the plurality of fixation points where the at least one marker is disposed in response to the load applied by the load simulation device, wherein the analysis system includes a digital image acquisition and processing component including two or more cameras for recording the position of the at least one marker in a 3D coordinate system and digital image correlation software for calculating a displacement vector of the at least one marker.

2. The system of claim 1, wherein the upper surface includes a coating to mimic a coefficient of friction between an abdominal wall and a textile-based implant.

3. The system of claim 1, wherein the fixation support includes a plurality of rods, each rod including a first end fixed to a lower surface of the tissue model that extends around the upper surface of the tissue model, and a second end terminating about or above the plane of the upper surface.

4. The system of claim 3, wherein the at least one marker is disposed on the second end of one or more of the plurality of rods.

5. The system of claim 3, wherein each rod of the plurality of rods is positioned in a 3D coordinate system in relation to a barycenter of the opening in the upper surface of the tissue model.

6. The system of claim 3, wherein each rod of the plurality of rods is uniformly spaced a predetermined distance apart from an adjacent rod of the plurality of rods and a predetermined distance from the upper surface of the tissue model.

7. The system of claim 1, wherein the at least one marker is disposed on the fixation support at fixation points positioned at two warp extremities of the textile-based implant.

8. The system of claim 1, wherein the load simulation device is a plunger including a spherical contacting surface.

9. The system of claim 8, wherein the plunger is configured to exert a force in a direction perpendicular to the plane of the upper surface of the tissue model.

10. The system of claim 1, wherein the analysis system includes mathematical software for calculating the shear force vector using the displacement vector of the at least one marker.

11. The system of claim 1, wherein the analysis system is configured to control the load simulation device.

12. The system of claim 11, wherein the analysis system is configured to calculate a bulge in the textile-based implant.

13. A system for assessing the distribution of shear forces at fixation points on a textile-based implant, the system comprising:
a tissue model including a base including a plurality of fixation rods configured to secure a textile-based implant thereto at a plurality of fixation points;
a load simulation device configured to apply a load to a textile-based implant secured to the tissue model; and,
an analysis system configured to calculate a shear force vector at each of the one or more of the plurality of fixation points in response to the load applied by the load simulation device, wherein the analysis system includes a digital image acquisition and processing component including two or more cameras for recording the position of the at least one marker in a 3D coordinate system and digital image correlation software for calculating a displacement vector of the at least one marker.

14. The system of claim 13, wherein the base further includes an upper surface extending along a plane and having a closed perimeter that defines an opening therethrough.

15. The system of claim 14, wherein the plurality of fixation rods each include a first end fixed to a lower surface of the base that extends around the upper surface of the base, and a second end terminating about or above the upper surface.

16. The system of claim 15, wherein the analysis system further includes at least one marker disposed on at least one of the plurality of fixation rods.

17. The system of claim 13, wherein the analysis system includes mathematical software for calculating the shear force vector using the displacement vector of the at least one marker.

* * * * *